(12) United States Patent
Indo et al.

(10) Patent No.: US 8,146,655 B2
(45) Date of Patent: Apr. 3, 2012

(54) METHODS AND APPARATUS FOR DOWNHOLE CHARACTERIZATION OF EMULSION STABILITY

(75) Inventors: Kentaro Indo, Edmonton (CA); Kai Hsu, Sugar Land, TX (US)

(73) Assignee: Schlumberger Technology Corporation, Sugar Land, TX (US)

(*) Notice: Subject to any disclaimer, the term of this patent is extended or adjusted under 35 U.S.C. 154(b) by 417 days.

(21) Appl. No.: 12/578,425

(22) Filed: Oct. 13, 2009

(65) Prior Publication Data

US 2011/0083842 A1   Apr. 14, 2011

(51) Int. Cl.
*E21B 49/08* (2006.01)
*E21B 47/00* (2006.01)

(52) U.S. Cl. ............ 166/250.01; 166/264; 73/152.24; 73/152.55; 250/256; 250/269.1

(58) Field of Classification Search ............ 166/250.01, 166/264; 73/152.24, 152.55; 250/255, 256, 250/268, 269.1
See application file for complete search history.

(56) References Cited

U.S. PATENT DOCUMENTS

| | | | |
|---|---|---|---|
| 4,860,581 A | 8/1989 | Zimmerman et al. |
| 4,936,139 A | 6/1990 | Zimmerman et al. |
| 5,783,826 A | 7/1998 | Meunier |
| 6,334,489 B1 | 1/2002 | Shwe et al. |
| 6,489,368 B2 | 12/2002 | Varadaraj et al. |
| 7,458,252 B2 | 12/2008 | Freemark et al. |
| 7,461,547 B2 | 12/2008 | Terabayashi et al. |
| 2006/0243033 A1 | 11/2006 | Freemark et al. |
| 2007/0035736 A1 | 2/2007 | Vannufelen et al. |
| 2007/0134804 A1 | 6/2007 | Fisher et al. |
| 2008/0257036 A1 | 10/2008 | Chaudoreille et al. |

FOREIGN PATENT DOCUMENTS

WO   WO2008095053 A1   8/2008

OTHER PUBLICATIONS

Narve Aske, Characterisation of Crude Oil Components, Asphaltene Aggregation and Emulsion Stability by means of Near Infrared Spectroscopy and Multivariate Analysis, Jun. 2002, Department of Chemical Engineering, Norwegian University of Science and Technology, Trondheim, Norway.

*Primary Examiner* — Giovanna Wright
(74) *Attorney, Agent, or Firm* — Jay P. Sbrollini; Wayne I. Kanak

(57) ABSTRACT

A method (and corresponding apparatus) for downhole fluid analysis of petroleum formation fluids. The method includes capturing in a chamber of a downhole tool at least two immiscible formation fluids in a generally segregated state (the fluids including petroleum), activating a fluid mixing means to mix the fluids in the chamber to create an emulsion therefrom, and allowing the emulsified fluids to segregate while measuring light transmittance through the segregating fluids in order to calculate a transition time period based on the light transmittance through the fluids in the chamber. The transition time period is preferably bounded by the time required for the light transmittance values measured by the light detector to reach a baseline light transmittance. The transition time period characterizes the stability of an emulsion formed by the captured fluids. The methods and apparatus can also be used for other fluid testing applications beyond downhole formation fluid testing.

30 Claims, 6 Drawing Sheets

METHODS AND APPARATUS FOR DOWNHOLE CHARACTERIZATION OF EMULSION STABILITY

BACKGROUND OF THE INVENTION

1. Field of the Invention

This disclosure relates generally to fluid analysis, and more particularly, to an apparatus and method for downhole analysis of formation fluids in a wellbore.

2. Description of Related Art

A fluid is a substance that continually deforms or flows under an applied pressure. It may contain liquids, gases, and solid particles, and generally takes on the shape of the container in which it is housed. When a fluid is transported through a pipe or tube, a number of properties of the fluid (such as temperature, pressure, and viscosity) may change depending on both the external constraints and the composition of the fluid. An emulsion is a fluid that consists of a mixture of at least two fluids that do not or only partially blend with each other. In a two-phase emulsion, one fluid (the dispersed phase) is dispersed within the other (the continuous phase). The creation of an emulsion from separate phases generally requires stirring, shaking, or some other form of energy input. The process by which emulsions are created is called emulsification.

Over time, the components of an unstable emulsion tend to separate if the mixing, stirring, or shaking is ceased. One common example of an emulsion that quickly separates is oil and vinegar salad dressing. When an oil and vinegar salad dressing bottle is shaken, the components of the salad dressing are temporarily dispersed. When the shaking ceases, the components separate. The stability of an emulsion is one of many important characteristics that can effect the operation and performance of an industrial device used to transport or in any way manipulate emulsions and/or the fluids which form them. As industrial devices frequently transport mixtures of oil, water, and/or other substances, it is generally known in the art to test certain characteristics of these and other fluids commonly found in various formations.

For example, wellbores are often drilled to locate and produce hydrocarbons such as crude oils ranging from very light to highly asphaltenic crudes. These crude oils are a continuum of tens of thousands of different hydrocarbon molecules having varying properties. Typical emulsions encountered in the petroleum industry include water droplets dispersed in the oil phase (W/O), and sometimes oil droplets dispersed in water (O/W), or oil droplets dispersed in water droplets that are in turn dispersed in a continuous oil phase (O/W/O). The emulsion forms as a result of the co-production of water from the oil reservoir. During processing, pressure gradients over chokes and valves introduce sufficiently high mechanical energy input (shear forces) to disperse water as droplets in the oil phase (*Characterization of Crude Oil Components, Asphaltene Aggregation and Emulsion Stability by means of Near Infrared Spectroscopy and Multivariate Analysis*, Narve Aske Dept. of Chemical Engineering, Norwegian University of Science and Technology, pages 5-10, June 2002). Water-in-crude oil emulsion destabilization basically involves three steps, namely, flocculation, followed by sedimentation of water droplets due to density differences, and finally coalescence of the individual water droplets. Emulsifying agents, such as scale, clay particles, added chemicals, or indigenous crude oil components like asphaltenes, resins, waxes, and naphthenic acids are typically present in varying quantities at the oil-water interface and hinder the coalescence process. The interaction with the asphaltenes is believed to be the main stabilizing effect on the emulsion (Id. at page 9).

During or subsequent to a drilling operation, it may be desirable to perform evaluations of the formations penetrated by the wellbore, which commonly contain varying quantities of oil and water. These evaluations may be performed by removing the drilling tool and deploying a wireline tool into the wellbore to test and sample the formation and the fluids therein. Alternatively, the drilling tool itself may be provided with devices to test and sample the surrounding formation and fluids without requiring removal of the drilling tool from the wellbore. The samples taken and/or the tests performed may be used, for example, to characterize the hydrocarbons present in the formation.

Evaluation of the formation often requires that fluids from the formation be drawn into the downhole tool for testing, evaluation, and sampling. To this end, devices such as probes may be extended from the downhole tool to establish fluid communication with the formation surrounding the wellbore and to draw fluids from the formation into the downhole tool. Fluids passing through the downhole tool may then be tested and analyzed to determine various parameters and/or properties. The information obtained with regard to the various properties of the hydrocarbon reservoir fluids, including the viscosity, density, and phase behavior of the fluids at reservoir conditions, may be used to evaluate potential reserves, determine expected flow parameters in porous media, and design completion, separation, treating, and metering systems, among others.

Additionally, samples of the fluids may be collected in the downhole tool and retrieved at the surface. The downhole tool stores the formation fluids in one or more sample chambers or bottles, and carries the samples to the surface, often while keeping the formation fluid pressurized. The fluids may then be sent to an appropriate laboratory for further analysis. Typical fluid analysis or characterization includes, for example, composition, properties, and phase behavior. Such analyses may also be performed at the wellsite using a transportable lab system.

BRIEF SUMMARY OF THE INVENTION

The present invention is directed to a downhole fluid analysis method (and corresponding apparatus) for generating and analyzing an emulsion. The method includes capturing in a chamber of a downhole tool at least two formation fluids in a generally segregated state. The fluids captured in the chamber are then mixed into an emulsified state by activating a means for circulating and mixing the fluids in the chamber. After emulsification, the emulsified fluids are allowed to segregate by deactivating the fluid circulating means. During the segregation, light is transmitted into the segregating fluids and light transmittance through the segregating fluids is measured by a light detector. The output of the light detector during segregation is used to derive a transition time period which characterizes the stability of the emulsion formed by the fluids captured in the chamber.

In one preferred embodiment, the above method is employed with a downhole fluid testing apparatus positioned within a wellbore. The apparatus includes a probe for drawing fluids from a formation adjacent the wellbore into a flow loop, at least one valve which is selectively opened and closed to guide the fluids into the flow loop and seal them within the flow loop, a means for circulating and mixing the fluids within the flow loop into an emulsified state (thus creating an emulsion in the flow loop if at least two fluid phases are present, e.g., a continuous phase and a dispersed phase), a light source for transmitting light into the fluids in the flow loop, and a light detector for measuring the light transmitted from the light source through the fluids. The apparatus also preferably includes additional devices for testing the fluids captured within the chamber, including a pressure control assembly in fluid communication with the flow loop for changing the volume or pressure of the fluids captured within the flow loop, first and second sensing means for measuring pressure, temperature, and/or density of the fluids, and a control unit operably coupled to the fluid mixing means, pressure control assembly, first and second sensing means, and light detector for controlling operation thereof to generate and test the emulsion.

Various fluid characteristics may thus be obtained through testing the fluids with the apparatus in both segregated and emulsified form.

DETAILED DESCRIPTION OF THE INVENTION

Figure 1:
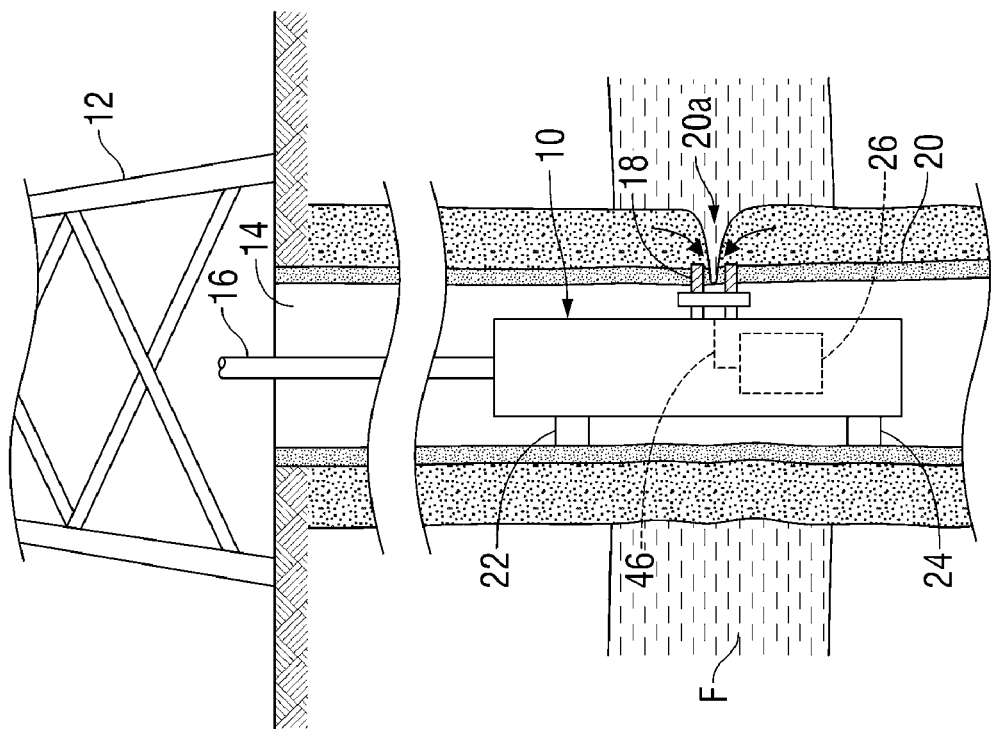
FIG. 1 is a schematic, partial cross-sectional view of a downhole wireline tool having an internal fluid analysis assembly with the wireline tool suspended from a rig.

Turning to FIG. 1, there is shown a schematic, partial cross-sectional view of an examplary downhole tool 10 suspended from a rig 12 into a wellbore 14. The downhole tool 10 can implement any type of downhole instruments capable of performing formation evaluation, such as fluid analysis, fluid sampling, or well logging. The downhole tool 10 of FIG. 1 is a wireline tool deployed from the rig 12 into the wellbore 14 via a wireline cable 16 and positioned adjacent to a formation F.

To seal the downhole tool 10 of FIG. 1 to a wall 20 of the wellbore 14 (hereinafter referred to as a "wall 20" or "wellbore wall 20"), the downhole tool 10 includes a probe 18. The probe 18 of FIG. 1 forms a seal with the wall 20 and draws fluid(s) from the formation F into the downhole tool 10 as depicted by the arrows 20a. Pistons 22 and 24 assist in pushing the probe 18 of the downhole tool 10 against the wellbore wall 20.

In accordance with the present invention, the downhole tool 10 of FIG. 1 includes a fluid analysis assembly 26 for downhole sampling and fluid analysis of formation fluid. The fluid analysis assembly 26 can include many of the components disclosed in U.S. patent application Ser. No. 12/137,058, which is incorporated herein by reference in its entirety. The fluid analysis assembly 26 is also capable of forming an emulsion from the sampled formation fluids, as well as evaluating/analyzing the emulsion for characterizing stability of the emulsion. The fluid analysis assembly 26 receives the formation fluid from the probe 18 via an evaluation flowline 46. The components of a preferred embodiment of the fluid analysis assembly 26 for use in the downhole tool 10 are described below in connection with FIGS. 3A-6.

Figure 2:
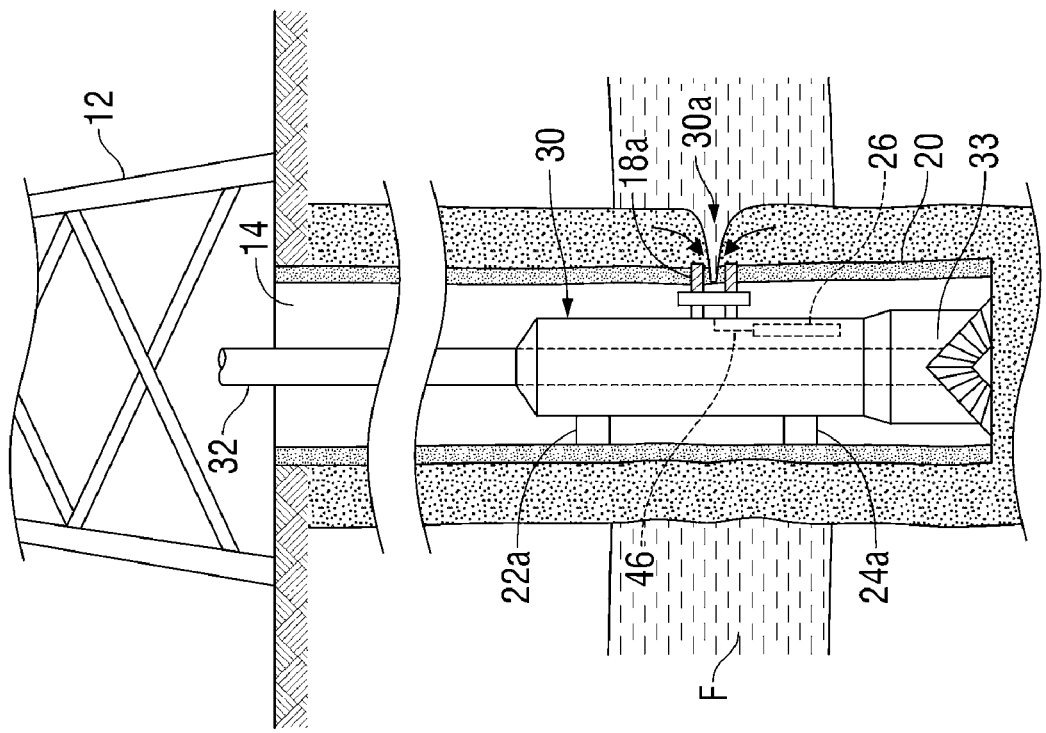
FIG. 2 is a schematic, partial cross-sectional view of a downhole drilling tool having an internal fluid analysis assembly with the downhole drilling tool suspended from a rig.

FIG. 2 shows a schematic, partial cross-sectional view of another example of a downhole tool 30. The downhole tool 30 of FIG. 2 can be conveyed among one or more of a measurement-while-drilling (MWD) tool, a logging-while-drilling (LWD) tool, or other downhole tool known to those skilled in the art. The downhole tool 30 is attached to a drill string 32 and a drill bit 33 driven by the rig 12 to form the wellbore 14.

To seal the downhole tool 30 of FIG. 2 to the wall 20 of the wellbore 14, the downhole tool 30 includes a probe 18a. The probe 18a of FIG. 2 forms a seal with the wall 20 and draws fluid(s) from the formation F into the downhole tool 30 as depicted by the arrows 30a. Pistons 22a and 24a assist in pushing the probe 18a of the downhole tool 30 against the wellbore wall 20. Drilling is stopped before the probe 18a is brought into contact with the wall 20.

To analyze fluid(s), the downhole tool 30 of FIG. 2 may include the same fluid analysis assembly 26 of FIG. 1. The fluid analysis assembly 26 of FIG. 2 performs formation evaluation and/or analysis of downhole fluids, such as the formation fluids extracted or drawn from the formation F. The fluid analysis assembly 26 receives the formation fluid(s) from the probe 18a via the evaluation flowline 46. The components of a preferred embodiment of the fluid analysis assembly 26 for use in the downhole tool 30 are described below in connection with FIGS. 3A-6.

Figure 3A:
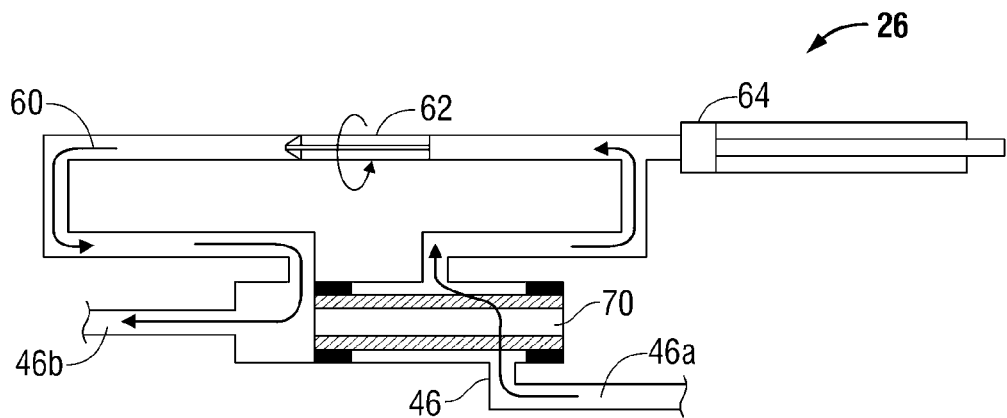
FIG. 3A illustrates several components of the fluid analysis assembly schematically represented in FIG. 1, including a valve and flow loop in an open position relative to the evaluation flowline.
Figure 3B:
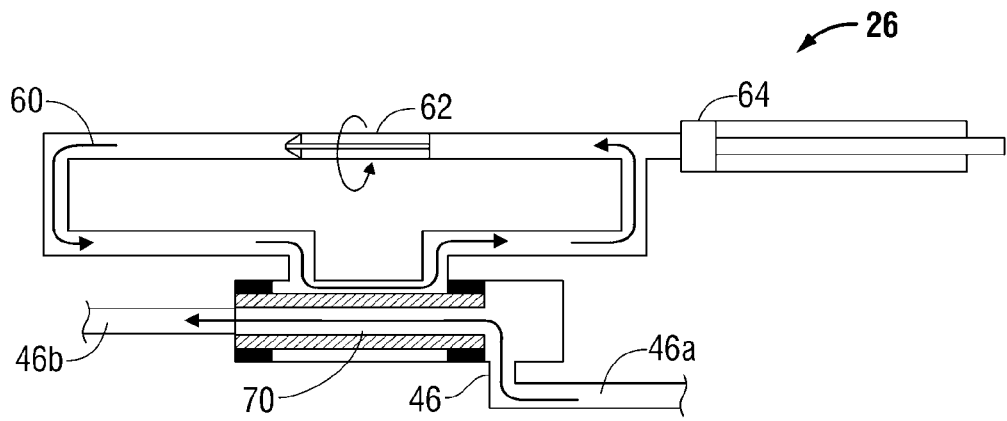
FIG. 3B illustrates the components of the fluid analysis assembly of FIG. 3A with the valve and flow loop in a closed position.

Turning now to FIGS. 3A-3B, there is shown several components of the fluid analysis assembly 26, including a flow loop 60, a circulation pump 62 for circulating and mixing fluids in the flow loop 60, a Pressure Volume Control Unit (PVCU) 64 for varying the pressure of the fluids in the flow loop 60, and a four port, two position valve 70. The valve 70 can be operated in an open position and a closed position. In the open position as shown in FIG. 3A, formation fluid(s) flowing through the evaluation flowline 46 are diverted into and captured by the flow loop 60. In the closed position as shown in FIG. 3B, formation fluid(s) flowing through the evaluation flowline 46 pass through the valve 70 without diverting into the flow loop 60. When the valve 70 is closed, the flow loop 60 forms a closed-loop system with the formation fluids trapped therein as shown in FIG. 3B. The flow loop 60 of FIGS. 3A-3B is a circular flow loop. Alternatively, other chamber types or vessel types can be used provided that the fluid chamber or vessel is capable of receiving or capturing fluids, permits sufficient agitation of the fluids to form an emulsion, and allows light to be transmitted through the fluids in the chamber and measured as further discussed below. The circulation pump 62 is preferably an impeller pump which can rotate up to 15,000 rpm, although a gear pump or a vane pump may also be used. The PVCU 64 is preferably similar to that disclosed in U.S. patent application Ser. No. 12/137,058, incorporated by reference above, and is further discussed below with respect to FIG. 6. The implementation of these components into downhole tool 10 and example methods of their use are further discussed below with respect to FIGS. 6-7E.

Figure 4:
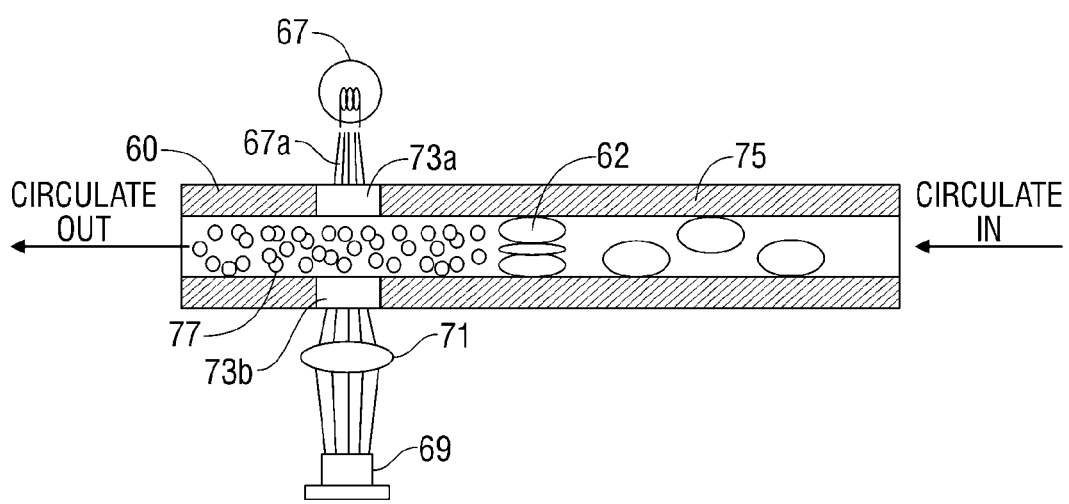
FIG. 4 illustrates the light source and light detector of the fluid analysis assembly, as well as the generation of an emulsion within the flow loop.
Figure 5A:
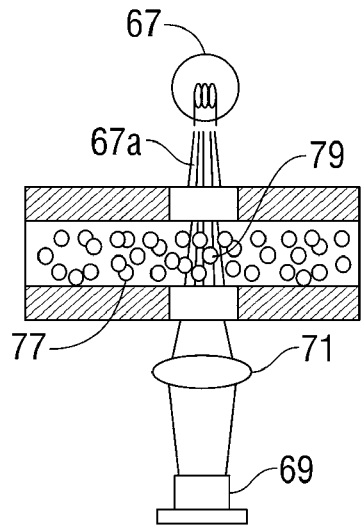
FIG. 5A illustrates the decreased transmittance of light from the light source caused by light scattering as a result of particles of the emulsion.

Turning now to FIG. 4, there is shown a portion of the flow loop 60 of FIGS. 3A-3B, as well as several additional components of the fluid analysis assembly 26, including a light source 67, a light detector 69, and an optical lens 71. The light source 67 transmits light 67a through the fluids in the flow loop 60. The light detector 69 measures the transmittance of light 67a transmitted by the light source 67 passing through the fluids in the flow loop 60 and received at the light detector 69. The optical lens 71 assists with light detection. Light 67a travels from the light source 67 through a first optical window 73a in the sidewall 75 of the flow loop 60, through the fluids disposed in the flow loop 60, through a second optical window 73b in the sidewall 75 of the flow loop 60, where it is collected by the optical lens 71 and directed to the light detector 69. In the event that the fluids captured within the flow loop 60 are two immiscible fluids (such as oil and water), circulation and mixing of the fluids by the circulation pump 62 mixes the fluids into an emulsified state and thus creates an emulsion 77 within the flow loop 60. The emulsion 77 scatters the light 67a transmitted from the light source 67 as shown schematically in FIG. 5A at reference number 79. Thus, when the fluids in the flow loop 60 are emulsified (FIG. 5A), the transmittance of light 67a from the light source 67 to the light detector 69 is decreased, causing a low output signal from the light detector 69 (FIGS. 5A, 5C).

When the circulation pump 62 is turned off, the two immiscible fluids (e.g. oil and water) of the emulsion begin to segregate. As the two fluids segregate, the scattering 79 of light 67a decreases. Thus, the transmittance of light 67a from the light source 67 to the light detector 69 gradually increases during segregation of the fluids, resulting in an increasing output signal from the light detector 69 as shown by the sloped portion of the graph of FIG. 5C. After a period of time, the fluids in the flow loop 60 will fully segregate and the output of the light detector 69 will return to its output signal level prior to fluid mixing as illustrated schematically in FIGS. 5B and 5C. The duration of this time period t, which is referred to as a "transition period" herein, is measured by the time it takes for the fluids of the emulsion to fully segregate once the circulation pump 62 is turned off. This transition period characterizes the stability of the emulsion, and is generally higher when the fluids of the emulsion are highly viscous, and vice versa. The implementation of these components into the downhole tool 10 is discussed below with respect to FIG. 6, and example methods of their use are further discussed below with respect to FIGS. 7A-7E.

It should be noted that light detector 69 may alternatively be located on the same side of the flow loop 60 as the light source 67. In this case the light detector 69 senses the backscatter of light 69a caused by the emulsion 77 and the interpretation is the opposite of that described above. Namely, a strong backscatter signal will be received in the emulsified stage, and a weak backscatter signal will be received in the segregated stage.

Figure 6:
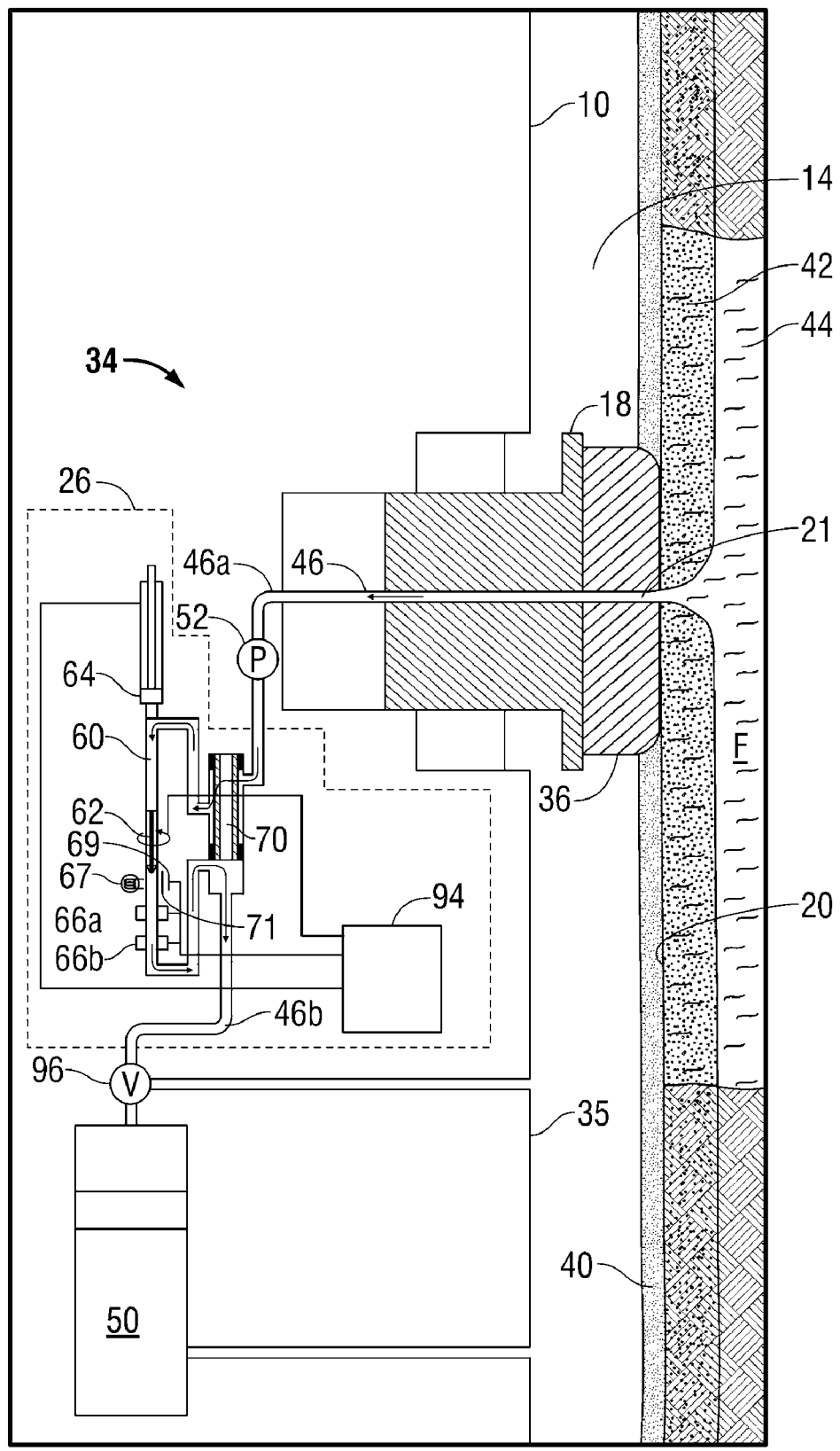
FIG. 6 illustrates an example manner of implementing any or all of the components of the fluid analysis assembly into the downhole wireline tool.

Turning now to FIG. 6, shown is shown an exemplary implementation of the various components of the fluid analysis assembly 26 integrated into the downhole tool 10 of FIG. 1. In an alternative embodiment, the fluid analysis assembly 26 can be integrated into the downhole tool 30 of FIG. 2 in a similar fashion. The probe 18 of FIG. 6 extends from a housing 35 of the downhole tool 10 for engagement with the wellbore wall 20. The probe 18 is provided with a packer 36 for sealing with the wellbore wall 20. The packer 36 contacts the wellbore wall 20 and forms a seal with a mud cake 40 lining the wellbore 14. The mud cake 40 gets deposited on the wellbore wall 20 due to seepage of mud and mud filtrate into the formation F. This seepage creates an invaded zone 42 about the wellbore 14. The invaded zone 42 contains mud filtrate and other wellbore fluids that contaminate the surrounding formations, including the formation F and a portion of the virgin fluid 44 contained therein. The probe 18 also provides an actuated mechanism that is inserted through the mud cake 40 into the formation to form an inlet 21 fluidly coupled to an evaluation flowline 46 for drawing formation fluids into the evaluation flowline 46. Other fluid communication devices suitable for drawing fluid into the evaluation flowline 46, such as probes and dual packers, can be used. Examples of such fluid communication devices are described in U.S. Pat. Nos. 4,860,581 and 4,936,139, incorporated herein by reference in their entireties.

The evaluation flowline 46 extends into the downhole tool 10 and is used to pass fluid(s), such as virgin fluid 44, into the downhole tool 10 for pre-test, analysis, and/or sampling. A first portion 46a of the evaluation flowline 46 extends to the inlet of the open four port-two position valve 70 of FIG. 3A, which is disposed at the start of the flow loop 60 as shown in FIG. 6. A second portion 46b of the evaluation flowline 46 extends from the outlet of the open valve 70, which is disposed at the end of the flow loop 60. The second portion 46b passes through or ends at a valve 96 which selectively fluidly couples the second portion 46b to a sample chamber 50.

In this manner, when the valve 70 is open as shown in FIG. 3A and FIG. 6, formation fluid is guided from the formation F through the first portion 46a of the evaluation flowline 46, through the flow loop 60, through the second portion 46b of the evaluation flowline 46, and into the sample chamber 50 disposed below or adjacent the flow loop 60. When the valve 70 is closed as shown in FIG. 3B, formation fluid is guided from the formation F through the first portion 46a of evaluation flowline 46 and directly to the second portion 46b for supply to the sample chamber 50 via the valve 70, without passing through the flow loop 60. When the valve 70 is closed, the fluid loop 60 forms a closed-loop system with the formation fluids trapped therein as shown in FIG. 3B. The fluid flow system 34 of FIG. 6 may also include a pump 52 to draw fluid through the first portion of the flowline 46a. While FIG. 6 shows an exemplary configuration of a downhole tool 10 used to draw fluid from the formation F, it will be appreciated by one of skill in the art that any number and/or type(s) of configurations of flowlines, pumps, sample chambers, valves and other devices may be used and that the configuration of FIG. 6 is not intended to limit the scope of the invention. For example, it is anticipated that a plurality of two position valves as shown in U.S. patent application Ser. No. 12/137,058 may be selectively opened and closed to achieve the same result.

The components of the fluid analysis assembly 26 described with respect to FIGS. 3A-5B can be implemented into the downhole tool 10 of FIG. 1 as shown schematically in FIG. 6. The assembly 26 includes the flow loop 60, circulation pump 62, PVCU 64, light source 67, light detector 69, valve 70, and lens 71, as well as one or more sensors (two of which are designated at reference numerals 66a and 66b), all of which may be used independently and/or collectively to test and measure the fluids downhole as well as generate and characterize an emulsion as described herein. Various other downhole tests and measurements, including phase measurements, viscosity measurements, density measurements, pressure measurements, and/or fluid compressibility determinations for the formation fluids may be performed using the fluid analysis assembly 26 according to the methods described in U.S. patent application Ser. No. 12/137,058.

As described above with respect to FIGS. 3A and 3B, the flow loop 60 of FIG. 6 is implemented as a bypass flowline communicating with the first and second portions 46a, 46b of the evaluation flowline 46 such that formation fluid(s) can be diverted into and captured by the flow loop 60 when the valve 70 is open (FIG. 3A). Alternatively, the fluids pass through the valve without diverting into the flow loop 60 when the valve 70 is closed (FIG. 3B). In general, for the sake of description, the flow loop 60 includes all flowlines positioned to the left of valve 70 in FIG. 6.

Circulation pump 62 circulates and mixes the fluid within the flow loop 60 to enhance the homogeneity of the fluids and enhance the accuracy of measurements obtained thereof, such as pressure/temperature and density via the sensor(s) 66a and/or 66b as described in U.S. patent application Ser. No. 12/137,058. Circulation pump 62 is also used to mix the fluids captured in the flow loop 60 into an emulsified state as described below in detail.

Preferably, PVCU 64 is used to change the pressure of the fluid(s) within the chamber 60 in a continuous or stepwise manner. The PVCU 64 can be any type of assembly or device capable of communicating with the flow loop 60 and continuously changing (and/or step-wise changing) the volume or pressure of the fluid(s) captured within the flow loop 60, including, but not limited to, that disclosed in U.S. patent application Ser. No. 12/137,058. The sensor 66a is any type of pressure sensing device capable of measuring and/or recording the pressure of the fluids captured in the flow loop 60. For example, the pressure sensing sensor 66a can be realized by a micro-sapphire sensor. The sensor 66b of FIG. 6 is any type of density sensor capable of measuring and/or determining the density of the fluid captured in the flow loop 60. For example, the density sensor 66b can be realized by a vibrating rod, and electronics for actuation and detection. Such a sensor is based on the principle of mechanically vibrating and resonating elements interacting with the fluid and is described in U.S. Patent Application Publication U.S. 2008/0257036, which is incorporated herein by reference. As is well known in the art, the resonance characteristic(s) of a vibrating rod oscillating in a fluid may used to measure, compute and/or otherwise detect the density of the fluid in which the vibrating rod oscillates.

Figure 5B:
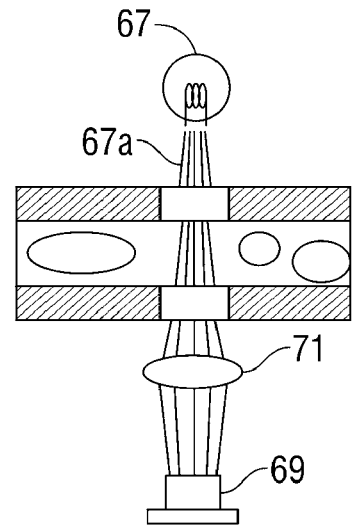
FIG. 5B illustrates the normal transmittance of light from the light source through the segregated fluids.
Figure 5C:
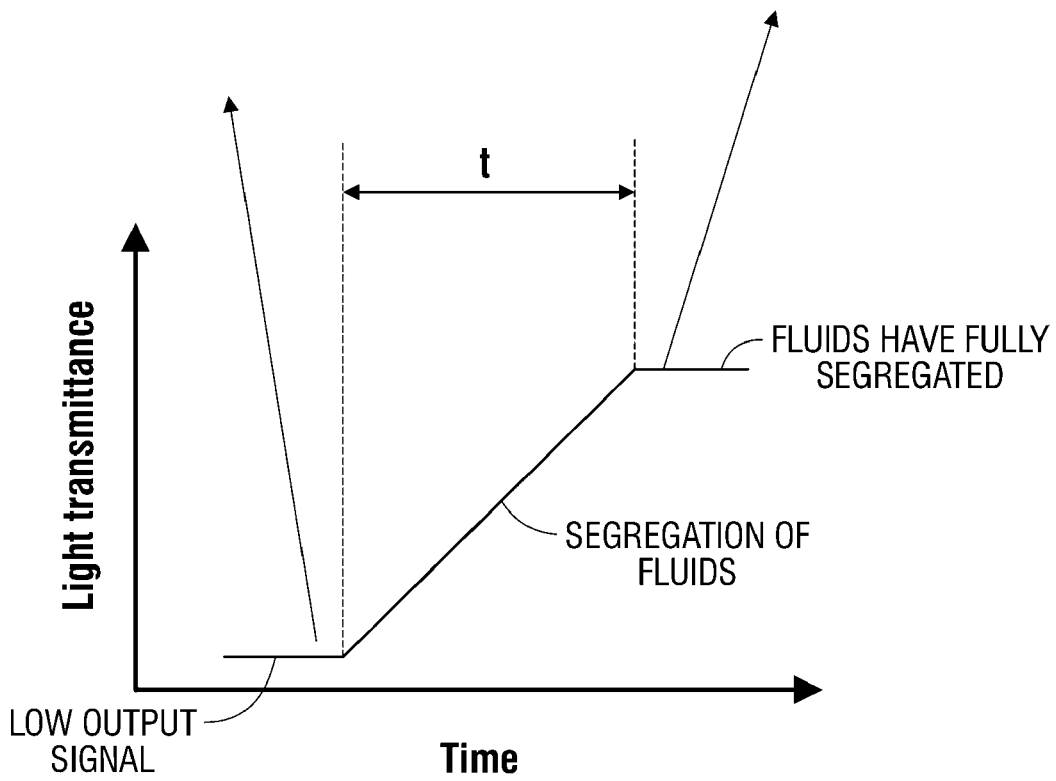
FIG. 5C is a graph depicting the light transmittance value output by the light detector as a function of time as the fluids segregate from an emulsified state to a segregated state.

The light source 67, light detector 69, and lens 71 of FIGS. 4-5B are also shown in FIG. 6 as part of the fluid analysis assembly 26 and operate as described above with respect to FIGS. 4-5C.

The fluid analysis assembly 26 of FIG. 6 is also preferably provided with a controller 94 which interfaces with and selectively operates the valve 70, circulating pump 62, PVCU 64, the sensor(s) 66a and 66b, the light source 67, and the light detector 69, which are collectively referred to herein as "testing devices." It is anticipated that the wiring, communications, and operational controls between the controller 94 and the testing devices may be the same or similar to that disclosed in U.S. patent application Ser. No. 12/137,058. The controller 94 interfaces with the testing devices for testing formation fluids captured within the flow loop 60. For example, the controller 94 may communicate with and control valve 70 to selectively divert formation fluid into the flow loop 60 in order to capture the formation fluid therein as discussed above. The controller 94 may also selectively operate the circulation pump 62 to generate an emulsion from the formation fluids captured within flow loop 60. The controller 94 may test the emulsion formed within the flow loop 60 by deactivating the circulation pump 62 and activating the light source 67 to derive data based on the output of the light detector 69 as the emulsion segregates. This data may include a plurality of light transmittance values representing light transmittance through the formation fluid over time, a plurality of time measurements corresponding to the plurality of light transmittance values, and calculations that use the plurality of light transmittance values and time measurements to determine a transition time period which characterizes the emulsion's stability as further discussed below with respect to FIGS. 7A-7E. The controller 94 may also control PVCU 64 to transition the fluid(s) captured in the flow loop 60 at or through a plurality of pressures and derive, record, and/or output additional data based on outputs of other of the testing devices as discussed in U.S. patent application Ser. No. 12/137,058.

The controller 94 can store and communicate the data (or results derived therefrom) to a surface-located module via data telemetry means as is well know in the art. The surface-located module can record the data (or results) as part of a log or provide for on-site or remote real-time analysis of the data (or results). The controller 94 can communicate with the surface-located module via any suitable communication link, such as a cable or wire communication link, an airway communication link, infrared communication link, microwave communication link, or the like.

Alternatively, the controller 94 can be provided remotely with respect to the downhole tool 10. For example, the controller 94 or signal processor can be provided at a monitoring station located at the wellsite, or located remotely from the wellsite. The controller 94 includes one or more electronic or optical device(s) known in the art capable of executing the logic to effect the control of the testing devices, as well as to collect, store, or manipulate information from the testing devices.

The controller 94 may be realized by one or more programmable general purpose processor(s), one or more digital signal processors(s), application specific integrated circuit(s) (ASICs), programmable logic device(s) (PLDs) and/or field programmable logic device(s) (FPLDs), etc.

The output signal of the light detector 69 may be filtered to remove unwanted high frequency components, such as noise, therein. Such filtering can be carried out in the analog domain by filter circuitry coupled between the light detector and controller 94. Alternatively, the filtering can be carried out in the digital domain by the controller 94.

Turning to FIGS. 7A-7E, shown are graphical representations of a sample simulation method/test performed using light source 67, optical lens 71, light detector 69, and other of the testing devices of the fluid analysis assembly 26 of FIG. 6. For purposes of clarity, the operations which generate and test the fluids and produce the outputs corresponding to the graphs of FIGS. 7A-7E are described herein as being performed by the controller 94, but it is to be understood that these operational steps may alternatively be manually performed, or may be performed both manually and via controller 94. Additionally, and as discussed above, the methods and tests disclosed herein may be performed downhole or in a transportable lab and/or at a fixed location.

Figure 7A:
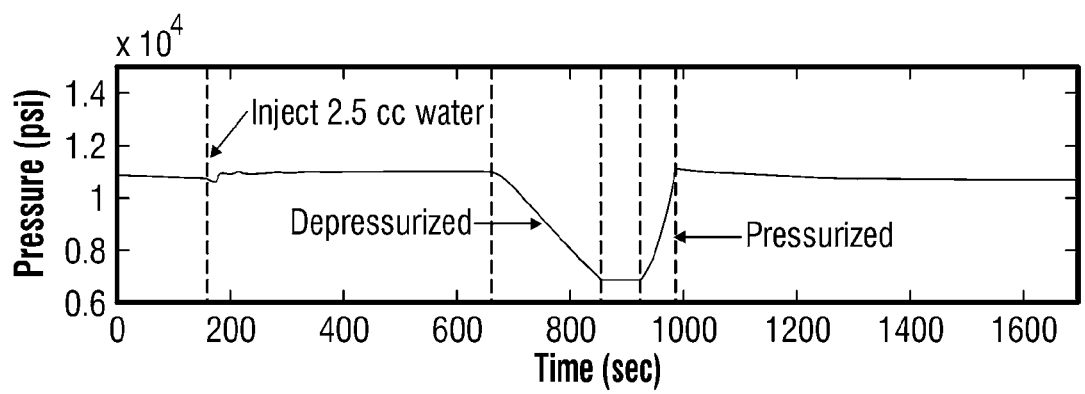
FIG. 7A is a graph illustrating the pressure of the fluids in the fluid analysis assembly over a test cycle time period.
Figure 7B:
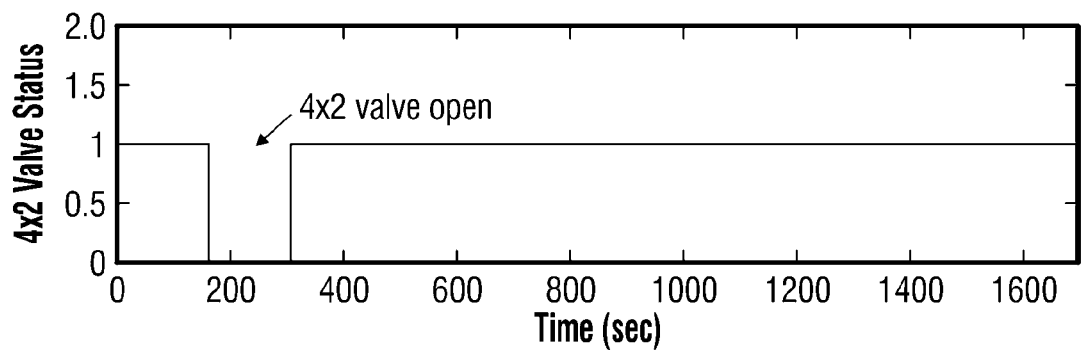
FIG. 7B is a graph illustrating the status of the valve of the fluid analysis assembly over the test cycle time period.

Turning now to FIG. 7B, between t=0 seconds and approximately t=160 seconds, controller 94 maintains valve 70 in the closed position. Between approximately t=160 seconds and approximately t=300 seconds, controller 94 maintains valve 70 in the open position to introduce formation fluids into flow loop 60. At approximately t=300 seconds, controller 94 switches valve 70 into the closed position to capture the formation fluids in flow loop 60. During the remaining test time, controller 94 maintains valve 70 in the closed position.

Figure 7C:
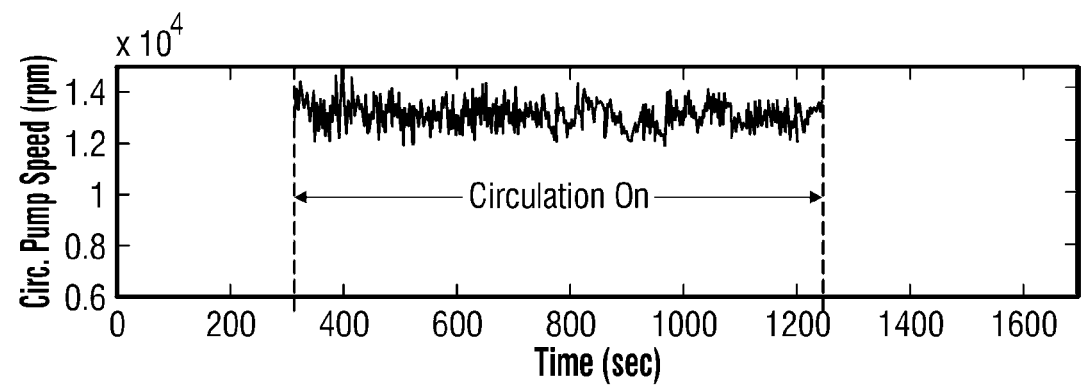
FIG. 7C is a graph illustrating the speed of the circulation pump of the fluid analysis assembly over the test cycle time period.
Figure 7D:
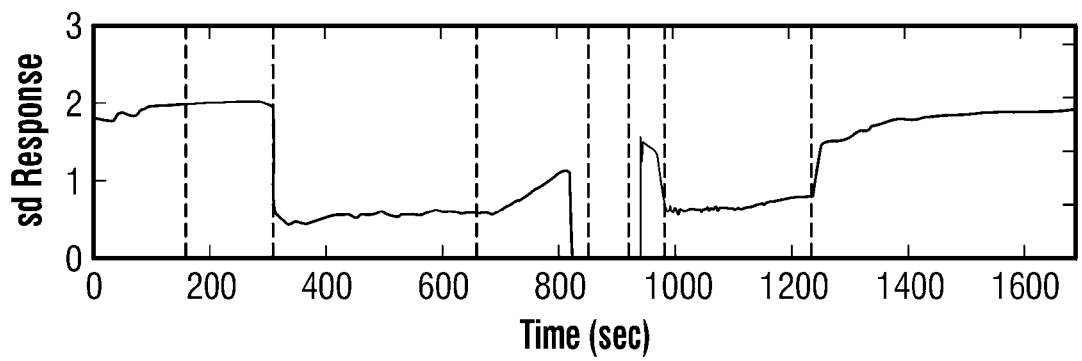
FIG. 7D is a graph illustrating the magnitude of the output signal generated by the light detector of the fluid analysis assembly over the test cycle time period.

Turning now to FIG. 7D, prior to opening valve 70 at approximately t=160 seconds, the fluid in flow loop 60 is already a mixture of oil and water. Therefore, one can see a gradual increase in light transmittance (scattering detector or sd Response, the ratio of light detector voltage over light source voltage) caused by segregation of the mixture before t=160 seconds. In the interval between t=160 and 300 seconds, where valve 70 is open, an additional 2.5 cc of water is charged into flow loop 60 (FIG. 7A). In this time interval, because circulation pump 62 is off (FIG. 7C), the water and oil in flow loop 60 remain segregated. The plateau sd Response level of 1.9 is therefore the baseline signal. In the example shown, the light transmittance (sd Response) through the fluids in flow loop 60 remains at a substantially constant value of approximately 1.9 for the period after valve 70 is opened. This sd Response value of 1.9 represents the baseline light transmittance value through the two fluids in flow loop 60 with the pressure at approximately 11,000 psi and the fluids in a segregated state.

Turning now to FIG. 7C, at approximately t=300 seconds controller 94 activates circulation pump 62 and maintains activation of circulation pump 62 for a duration of approximately 940 seconds. In the event that the formation fluid contains multiple phases, such operations effectively mix and circulate the formation fluids in flow loop 60 into an emulsified state, thereby forming an emulsion in the flow loop 60. Note that in the example shown, the mixing of the formation fluids by circulation pump 62 causes the light 67a transmitted by the light source 67 through the fluid to scatter (FIG. 5A) and thus reduces the light transmittance signal detected by light detector 69. An emulsion forms very quickly, and it is believed that the slight rise of the output signal from light detector 69 between approximately t=360 seconds and t=650 seconds is due to the system reaching equilibrium in flow loop 60. The initial noise component of the light transmittance value detected by light detector 69 is believed to be caused by the initial agitation of circulation pump 62. Once the flow of the fluids in flow loop 60 reaches a steady state flow distribution with the fluids fully emulsified, the light transmittance value levels off at about 0.5. Thus, the light transmittance value falls from the baseline transmittance value of 1.9 for the segregated fluids to approximately 0.5 for the emulsified fluids.

Figure 7E:
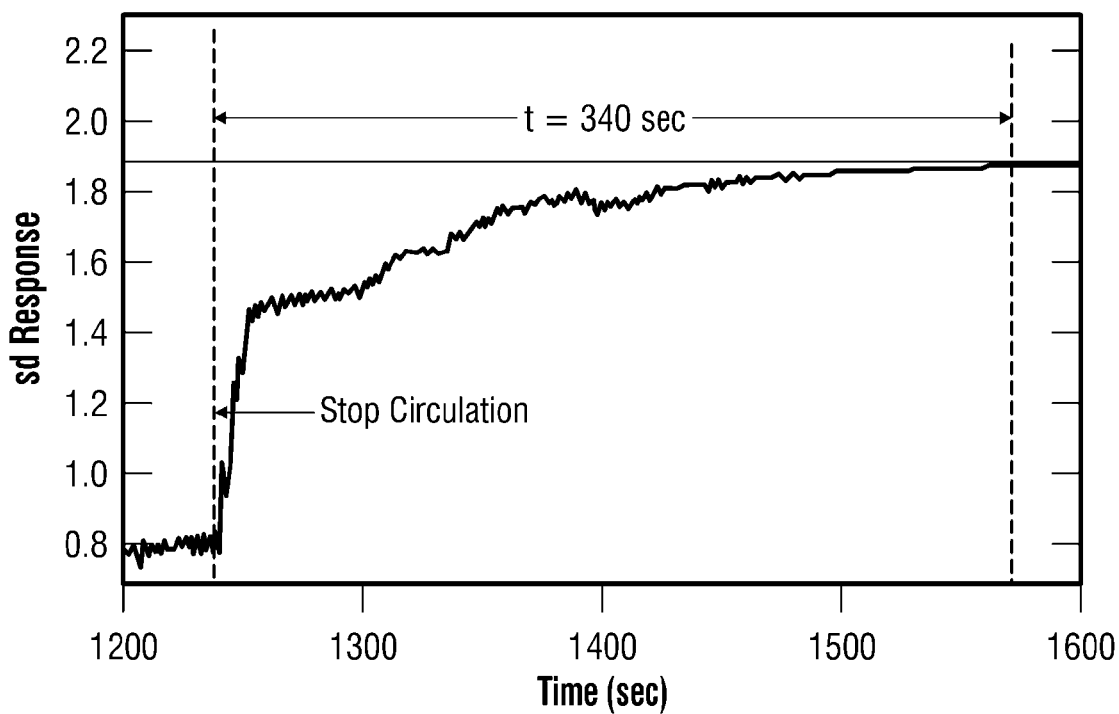
FIG. 7E is an enlarged view of the transition portion of the graph of FIG. 7D in which the output signal generated by the light detector illustrates the transition of the fluids in the flow loop from an emulsion state to a complete segregation state.

Turning now to FIG. 7D, synchronous with deactivation of circulation pump 62 at approximately t=1240 seconds, controller 94 starts a timer and also begins monitoring the output signal of light detector 69, thereby deriving light transmittance values from the monitored output signal over time. Upon deactivation of the circulation pump 62, the fluids of the emulsion begin to separate, in a process known as segregation. This segregation is indicated by the increased light transmittance values after deactivation of the circulation pump. As the fluids segregate, less light 67a is scattered. The controller 94 monitors the output signal of light detector 69 over time to ascertain if the light transmittance value output by the detector reaches the baseline transmission value. If so, controller 94 stops the timer and records the expired time measured by the timer as the transition time period for the emulsion. In the example shown, the transition time period is on the order of 340 seconds, and extends between t=1240 seconds and t=1580 seconds. At t=1580 seconds, the light transmittance value reaches the baseline value of 1.9 derived between t=160 seconds and t=300 seconds. FIG. 7E is an enlarged view of this transition time period portion of the graph of FIG. 7D (after t=1240 seconds). Alternatively, the transition time period for the emulsion may be established by the time required for the rate of change in the measured light transmittance to decrease to a predetermined value.

The transition time period as measured herein is an important parameter which may be used to characterize and estimate the emulsion's stability when fluids which form the emulsion are transported out of the downhole formation with various industrial equipment devices.

It is also anticipated that controller 94 may simply output the light transmittance values output by the light detector (or data derived therefrom) and possibly time data corresponding thereto. The light transmittance values may be sampled at a predetermined sampling rate and thus the time periods associated with the light transmittance value can be derived from the sampling rate. Such data can be output as a log accessible by a user via a printout and display for derivation of the transition time period for the emulsion.

Additionally, it is anticipated that the output response of the light detector 69 in conjunction with the pressure and pump speed values over time, all of which are illustrated in FIGS. 7A-7D, may be used to assess the saturation point of the emulsion (where it returns to the baseline sd Response level), the effect of varying pump speeds on the formation of the emulsion at different pressures, and other parameters.

For example, turning now to the portions of the graphs of FIGS. 7A-7D between t=650 seconds and t=1250 seconds, at approximately t=650 seconds, controller 94 activates PVCU 64 to continually depressurize flow loop 60 until about t=850 seconds (FIG. 7A). FIG. 7D shows that this depressurization causes the output signal of light detector 69 to steadily increase until about t=805 seconds. The increased output signal of light detector 69 between t=650 seconds and t=800 seconds is caused by the decreased concentration or density of the fluids in flow loop 60 (characterized by the Beer-Lambert law). At about t=805 seconds, the saturation pressure (e.g., bubble point or dew point) of the fluid emulsion in flow loop 60 is reached as illustrated in FIG. 7D, wherein the output signal of light detector 69 drops to zero. This occurs because the pressure at about t=805 seconds has dropped so low that gas bubbles come out of the fluid. Light transmission through the fluids is scattered by the gas bubbles and the emulsified droplets in the fluid, which causes the output signal of light detector 69 to decrease rapidly.

Turning back to FIG. 7A, the pressure is kept at a constant minimum from about t=850 seconds to t=910 seconds, and then continuously increased from about t=910 seconds to about t=990 seconds, where it again reaches the initial pressure of 11,000 psi. As shown in FIG. 7D, the light transmittance value derived from the output signal of light detector 69 jumps from zero to about 1.5 at about t=990 seconds. This occurs because at that point, the pressure in flow loop 60 (which had been steadily increased after t=910 seconds) is high enough to compress the gas bubbles back into the fluid, which eliminates or significantly reduces the scattering effect on the light caused by the gas bubbles. The further increase in pressure (FIG. 7A) in flow loop 60 between t=930 seconds and t=990 seconds causes the output signal (FIG. 7D) of light detector 69 to decrease on account of the increased density of the fluids, which decreases the transmittance of light therethrough until the pressure reaches the initial 11,000 psi level, at which point the light transmittance value reaches the same level (about 0.5) as prior to the depressurization of the fluids.

The device disclosed herein may be used to calculate the transition period with or without the additional variable of modifying the pressure within the fluids in flow loop 60. As long as the pressure in flow loop 60 when the baseline is calculated (prior to turning on circulation pump 62) is the same as the pressure in flow loop 60 when circulation pump 62 is turned off, the transition period observed as the time for the output of light detector 69 to reach the baseline level after deactivating circulation pump 62 will be the same and the system will give an accurate measure of emulsion stability at the reservoir pressure.

It is also anticipated that a flowline imager capable of capturing visual images of the fluids, measuring the distance between particles of the fluids from the captured images, and determining the volume fraction of the fluids may be implemented along with the other of the testing devices.

While the fluid analysis assembly 26 is described herein as part of a downhole fluid analysis tool, the fluid analysis assembly 26 may also be provided or implemented at the wellsite, or at an offsite facility for performing fluid tests. In such a configuration, the fluid analysis assembly 26 may be positioned in a housing that is transportable to a desired location. Alternatively, fluid samples may be taken to a surface or offsite location and tested with the fluid analysis assembly 26 at such a location. Data and test results from various locations may be analyzed and compared.

There have been described and illustrated herein several embodiments of a methodology (and corresponding apparatus) for downhole fluid analysis of formation fluid that generates an emulsion from such formation fluid and characterizes stability of the emulsion. While particular embodiments of the invention have been described, it is not intended that the invention be limited thereto, as it is intended that the invention be as broad in scope as the art will allow and that the specification be read likewise.

What is claimed is:

1. A method for downhole analysis of petroleum formation fluids comprising:
    (a) providing a chamber in a downhole tool suspended in a wellbore;
    (b) capturing in the chamber at least two immiscible fluids in a generally segregated state, the at least two fluids including petroleum fluid;
    (c) emulsifying the fluids in the chamber by activating a fluid mixing means for mixing the fluids;
    (d) allowing the emulsified fluids to segregate by deactivating the mixing means;
    (e) transmitting light into the fluids in the chamber and measuring light transmittance values through the fluids over time during (d); and
    (f) calculating the duration of a transition time period based upon the light transmittance values measured in (e), the transition time period beginning at the time of deactivation of the fluid mixing means, and the transition time period ending at a time determined by a change in the light transmittance values measured in (e).

2. A method according to claim 1, further comprising:
    (g) transmitting light into the fluids in the generally segregated state as captured in (b) and measuring light transmittance through the fluids to derive a baseline light transmittance; and
    wherein the transition time period of (f) ends in the event that the light transmittance measured in (e) reaches the baseline light transmittance derived at step (g).

3. A method according to claim 2, wherein the baseline light transmittance is derived from light transmittance values measured during (g) with the mixing means deactivated.

4. A method according to claim 1, further comprising:
    (g) calculating the rate of change of the light transmittance values measured in (e); and
    wherein the transition time period of (f) ends in the event that the rate of change of the light transmittance values calculated in (g) decreases to a predetermined value.

5. A method according to claim 1, wherein the chamber comprises a circulating flow loop housed within the downhole tool, and the fluid mixer means mixes and circulates fluids in the circulating flow loop.

6. A method according to claim 1, further comprising:
    (g) outputting or storing the transition time period duration calculated in (f) for characterizing emulsion stability for the fluids captured in (b).

7. A method according to claim 1, wherein the transmitting of light into the fluids and the measuring of light transmittance through the fluids during (e) is accomplished with a light source and light detector disposed on opposite sides of the chamber.

8. A method according to claim 1, further comprising inputting formation fluid into the chamber via a flowline fluidly coupled to a probe for drawing formation fluid into the flowline.

9. A method according to claim 1, wherein the transmitting of light into the fluids and the measuring of light transmittance through the fluids during (e) is accomplished with a light source and light detector disposed on the same side of the chamber.

10. A method for downhole analysis of petroleum formation fluids comprising:
    (a) providing a chamber in a downhole tool suspended in a wellbore;
    (b) capturing in the chamber at least two immiscible fluids in a generally segregated state, the at least two fluids including petroleum fluid;
    (c) emulsifying the fluids in the chamber by activating a fluid mixing means for mixing the fluids;
    (d) allowing the emulsified fluids to segregate by deactivating the mixing means;
    (e) transmitting light into the fluids in the chamber and measuring backscattered light from the fluids over time during (d); and
    (f) calculating the duration of a transition time period based upon the backscattered light values measured in (e), the transition time period beginning at the time of deactivation of the fluid mixing means, and the transition time period ending at a time determined by a change in the backscattered light values measured in (e).

11. An apparatus for downhole fluid testing of petroleum fluid, the apparatus comprising:
    a housing positionable within a wellbore adjacent a formation containing petroleum fluid, the housing supporting a chamber, a probe, at least one valve, fluid mixing means, a light source, a light detector, and a control unit;
    the probe for drawing at least two generally segregated fluids from the formation into the chamber, the two fluids including petroleum fluid;
    the at least one valve for sealing the fluids in the chamber;
    the fluid mixing means for mixing the fluids in the chamber into an emulsified state;

the light source for transmitting light into the fluids in the chamber;

the light detector for measuring the transmittance of light from the light source through the fluids in the chamber; and the control unit operably coupled to the fluid mixing means and the light detector, the control unit adapted to deactivate the fluid mixing means in order to allow the emulsified fluids to segregate, and the control unit including means for measuring light transmittance values output by the light detector over time while the fluid mixing means is deactivated in order to calculate a transition time period for the fluids captured in the chamber, whereby the duration of the transition time period characterizes emulsion stability for the fluids captured in the chamber.

12. An apparatus according to claim 11, wherein the control unit comprises means for calculating the duration of the transition time period based upon the light transmittance values measured while the fluid mixing means is deactivated.

13. An apparatus according to claim 11, wherein the control unit communicates the light transmittance values to another data processing system that calculates duration of the transition time period based upon the light transmittance values communication from the control unit.

14. An apparatus according to claim 11, wherein:
the control unit outputs the light transmittance values to another data processing system for logging and analysis.

15. An apparatus according to claim 11, wherein the transition time period begins at the time of deactivation of the fluid mixing means, and the transition time period ends at a time determined by a change in the light transmittance values output by the light detector.

16. An apparatus according to claim 15, wherein:
the control unit is adapted to measure light transmittance through the fluids captured in the chamber to derive a baseline light transmittance; and
the transition time period ends in the event that the light transmittance measured while the fluid mixing means is deactivated to allow for segregation reaches the baseline light transmittance.

17. An apparatus according to claim 16, wherein the baseline light transmittance is derived from light transmittance values measured with the fluid mixing means deactivated.

18. An apparatus according to claim 15, wherein:
the control unit is adapted to measure light transmittance through the fluids captured in the chamber; and
the transition time period ends in the event that the rate of change of the light transmittance decreases to a predetermined value.

19. An apparatus according to claim 11, wherein the chamber comprises a circulating flow loop, and the fluid mixer means mixes and circulates fluids in the circulating flow loop.

20. An apparatus according to claim 11, further comprising a pressurization assembly in fluid communication with the chamber and capable of changing the pressure of the fluids in the chamber.

21. An apparatus according to claim 20, wherein the control unit is operably coupled to the pressurization assembly for operation thereof.

22. An apparatus according to claim 11, further comprising a first sensing means for measuring at least one of temperature and pressure of fluids captured in the chamber.

23. An apparatus according to claim 22, further comprising a second sensing means for measuring density of fluids in the chamber.

24. An apparatus for downhole fluid testing of petroleum fluid, the apparatus comprising:
a housing positionable within a wellbore adjacent a formation containing petroleum fluid, the housing supporting a chamber, a probe, at least one valve, fluid mixing means, a light source, a light detector, and a control unit;
the probe for drawing at least two generally segregated fluids from the formation into the chamber, the two fluids including petroleum fluid;
the at least one valve for sealing the fluids in the chamber;
the fluid mixing means for mixing the fluids in the chamber into an emulsified state;
the light source for transmitting light into the fluids in the chamber;
the light detector for measuring the backscatter of light from the fluids in the chamber; and
the control unit operably coupled to the fluid mixing means and the light detector, the control unit adapted to deactivate the fluid mixing means in order to allow the emulsified fluids to segregate, and the control unit including means for measuring light backscatter values output by the light detector over time while the fluid mixing means is deactivated in order to calculate a transition time period for the fluids captured in the chamber, whereby the duration of the transition time period characterizes emulsion stability for the fluids captured in the chamber.

25. A fluid testing apparatus, comprising:
a chamber;
a probe for drawing at least two generally segregated immiscible fluids into the chamber;
at least one valve for sealing the fluids in the chamber;
fluid mixing means for mixing the fluids in the chamber into an emulsified state;
a light source for transmitting light into the fluids in the chamber;
a light detector for measuring transmittance of light from the light source through the fluids in the chamber; and
a control unit operably coupled to the fluid mixing means and the light detector, the control unit adapted to deactivate the fluid mixing means in order to allow the emulsified fluids to segregate, and the control unit including
means for measuring light transmittance values output by the light detector over time while the fluid mixing means is deactivated, and
means for calculating the duration of the transition time period based upon the light transmittance values measured while the fluid mixing means is deactivated.

26. A fluid testing apparatus according to claim 25, wherein the transition time period begins at the time of deactivation of the fluid mixing means, and the transition time period ends at a time determined by a change in the light transmittance values output by the light detector.

27. A fluid testing apparatus according to claim 26, wherein:
the control unit is adapted to measure light transmittance through the fluids captured in the chamber to derive a baseline light transmittance; and
the transition time period ends in the event that the light transmittance measured while the fluid mixing means is deactivated to allow for segregation reaches the baseline light transmittance.

28. A fluid testing apparatus according to claim 27, wherein the baseline light transmittance is derived from light transmittance values measured with the fluid mixing means deactivated.

29. A fluid testing apparatus according to claim 26, wherein:

the control unit is adapted to measure light transmittance through the fluids captured in the chamber to derive the rate of change of the light transmittance; and the transition time period ends in the event that the rate of change of the light transmittance measured while the fluid mixing means is deactivated to allow for segregation decreases to a predetermined value.

30. A fluid testing apparatus according to claim 25, wherein the chamber comprises a circulating flow loop, and the fluid mixer means mixes and circulates fluids in the circulating flow loop.

* * * * *